(12) United States Patent
Mittal et al.

(10) Patent No.: US 8,551,942 B2
(45) Date of Patent: Oct. 8, 2013

(54) LYOPHILIZED ANTI-FUNGAL COMPOSITIONS

(71) Applicant: Merck Sharp & Dohme Corp., Rahway, NJ (US)

(72) Inventors: Sachin Mittal, Bridgewater, NJ (US); Hossain Jahansouz, Burlingame, CA (US); Sutthilug Sottivirat, Lansdale, PA (US)

(73) Assignee: Merck Sharp & Dohme, Corp., Rahway, NJ (US)

( * ) Notice: Subject to any disclaimer, the term of this patent is extended or adjusted under 35 U.S.C. 154(b) by 0 days.

(21) Appl. No.: 13/628,592

(22) Filed: Sep. 27, 2012

(65) Prior Publication Data

US 2013/0023462 A1  Jan. 24, 2013

Related U.S. Application Data

(62) Division of application No. 12/666,426, filed as application No. PCT/US2008/007810 on Jun. 23, 2008, now abandoned.

(60) Provisional application No. 60/937,360, filed on Jun. 26, 2007.

(51) Int. Cl.
  *A01N 37/18* (2006.01)
  *A61K 38/12* (2006.01)
  *A61P 31/10* (2006.01)

(52) U.S. Cl.
  USPC ...................................................... 514/3.6

(58) Field of Classification Search
  None
  See application file for complete search history.

(56) References Cited

U.S. PATENT DOCUMENTS

| | | | |
|---|---|---|---|
| 5,378,804 A | 1/1995 | Balkovec et al. | |
| 5,514,650 A | 5/1996 | Balkovec et al. | |
| 5,552,521 A | 9/1996 | Belyk et al. | |
| 5,952,300 A | 9/1999 | Nerurkar et al. | |
| 6,136,783 A | 10/2000 | Neururkar et al. | |
| 6,960,564 B2 * | 11/2005 | Milton et al. | 514/3.3 |
| 8,232,245 B2 * | 7/2012 | Welz et al. | 514/3.6 |
| 2004/0185524 A1 | 9/2004 | Crowe et al. | |
| 2005/0147567 A1 | 7/2005 | Kuo et al. | |

FOREIGN PATENT DOCUMENTS

| | | |
|---|---|---|
| WO | 2005105978 A2 | 11/2005 |
| WO | WO 2006/026592 A2 | 3/2006 |
| WO | WO 2007/021970 A2 | 2/2007 |

OTHER PUBLICATIONS

Bowman et al. The Antifungal Echinocandin Caspofungin Acetate Kills Growing Cells of *Aspergillus fumigatus* in Vitro. Antimicrobial Agents and Chemotherapy. Sep. 2002. vol. 46, No. 9, pp. 3001-3012.*

Rybowicz et al. Caspofungin: the first agent available in the echinocandin class of antifungals. Proc (Bayl Univ Med Cent). Jan. 2002; vol. 15, No. 1, pp. 97-99.*

"Freeze-Drying (Lyophilization)," in Remington—The Science and Practice of Pharmacy 21st edition, 828-831 (David B. Troy ed., Lippincott Williams & Wilkins 2006).

Xiaolin (Charlie) Tank & Michael J. Pikal, "Design of Freeze-Drying Processes for Pharmaceuticals: Practical Advice," 21(2) Pharmaceutical Research 191-200 (Feb. 2004).

"Intravenous Infusion (not for IV Bolus Injection) CANCIDAS® (caspofungin acetate) for Injection" in Physician's Desk Reference (2007), printed Jan. 10, 2007.

Liuquan Chang et al., Effect of Sorbitol and Residual Moisture on the Stability of Lyophilized Antibodies: Implications for the Mechanism of Protein Stabilization in the Solid State, 94(7) J. Pharm. Sci. 1445-55 (2005).

C.C. Hsu et al., Determining the Optimum Residual Moisture in Lyophilized Protein Pharmaceuticals, 74 Develop. Biol. Standard. 255-271 (1991).

* cited by examiner

*Primary Examiner* — Marcela M Cordero Garcia
(74) *Attorney, Agent, or Firm* — Julie M. Lake; Sheldon O. Heber

(57) ABSTRACT

A lyophilized anti-fungal composition comprises (A) caspofungin, or a pharmaceutically acceptable salt thereof, in an effective amount; (B) one or more non-reducing sugars having a glass transition temperature $T_g(s)$ of at least about 90° C.; and (C) an acetate buffer in an amount effective to provide a pH in a range of from about 5 to about 7; wherein the weight ratio of the one or more non-reducing sugars to caspofungin is in a range of from about 1.1:1 to about 10:1; the composition has a moisture content of about 0.8 wt. % or less; and the composition has a glass transition temperature $T_g(c)$ of at least about 55° C. The lyophilized composition has good storage stability at temperatures up to and including room temperature. The composition can be reconstituted for use in preventing or treating fungal infections.

27 Claims, No Drawings

LYOPHILIZED ANTI-FUNGAL COMPOSITIONS

CROSS-REFERENCE TO RELATED APPLICATIONS

This application is a division of U.S. patent application Ser. No. 12/666,426, filed Dec. 23, 2009, which is a National Stage application of International Patent Application No. PCT/US2008/007810, filed Jun. 23, 2008. This application also claims priority to U.S. Provisional Patent Application No. 60/937,360, filed Jun. 26, 2007.

FIELD OF THE INVENTION

The invention is directed to caspofungin-containing pharmaceutical compositions useful for treating and/or preventing fungal infections.

BACKGROUND OF THE INVENTION

Caspofungin is a macrocyclic lipopeptide echinocandin whose structural formula is disclosed in column 2, lines 32-52 of U.S. Pat. No. 5,952,300. Caspofungin is also described in U.S. Pat. No. 5,378,804, and methods for its preparation are described in U.S. Pat. No. 5,378,804, U.S. Pat. No. 5,552,521, U.S. Pat. No. 5,952,300 and U.S. Pat. No. 6,136,783. Caspofungin is an inhibitor of the synthesis of $\beta$-(1,3)-D-glucan, which is an integral part of the fungal cell wall. Caspofungin is useful as an antibiotic, especially as an antifungal agent or as an antiprotozoal agent. As an antifungal agent, it is useful for the control of both filamentous fungi and yeast. It is especially adaptable to be employed for the treatment of mycotic infections in mammals, especially those caused by *Candida* species such as *C. albicans, C. tropicalis, C. krusei, C. glabrata* and *C. pseudotropicalis*, and *Aspergillus* species such as *A. fumigatus, A. flavus* and *A. niger*. In particular, the compound has been found effective against putatively Amphotericin B- and Fluconazole-resistant *Candida* isolates. The compound is also useful for the treatment and/or prevention of *Pneumocystis carinii* pneumonia to which immune compromised patients, such as those suffering from AIDS, are especially susceptible.

Caspofungin is typically employed in a lyophilized composition that is reconstituted for intravenous infusion. Preferred lyophilized caspofungin compositions are acetate-buffered products such as those described in U.S. Pat. No. 5,952,300. Of particular interest is the lyophilized, acetate-buffered product containing caspofungin in the form of a diacetate salt, sucrose, mannitol, glacial acetic acid, and sodium hydroxide. Such a product is available from Merck & Co., Inc. under the trade name CANCIDAS in 35 mg, 50 mg, and 70 mg doses. CANCIDAS is indicated for empirical therapy for fungal infection in patients with fever and neutropenia, the treatment of Candidemia and certain other *Candida* infections, the treatment of esophageal Candidiasis, and the treatment of invasive Aspergillosis in patients who are resistant to or cannot tolerate other therapies.

Lyophilized, acetate-buffered, caspofungin products such as CANCIDAS are characterized by good storage stability at low temperature (e.g., 2° C. to 8° C.) under ambient storage conditions. More particularly, the compositions can be stored at low temperature (e.g., 5° C.) for many months with minimal formation of degradates. Nonetheless, lyophilized caspofungin-containing products with improved storage stability at low temperatures and/or satisfactory storage stability at higher temperatures is desirable. Improved storage stability at about 5° C. would provide for a longer shelf life thereby reducing the potential for product loss. Satisfactory storage stability at room temperature would eliminate the need for refrigeration and the special handling and extra costs associated therewith.

SUMMARY OF THE INVENTION

The present invention includes a lyophilized anti-fungal composition which comprises:
(A) caspofungin, or a pharmaceutically acceptable salt thereof, in an effective amount;
(B) one or more non-reducing sugars having a glass transition temperature $T_g(s)$ of at least about 90° C.; and
(C) an acetate buffer in an amount effective to provide a pH in a range of from about 5 to about 7;
wherein:
the weight ratio of the one or more non-reducing sugars to caspofungin is in a range of from about 1.1:1 to about 10:1;
the composition has a moisture content of about 0.8 wt. % or less; and
the composition has a glass transition temperature $T_g(c)$ of at least about 55° C.

The lyophilized anti-fungal composition of the present invention has good chemical and storage stability at and below room temperature (i.e., at or below about 30° C.). The composition typically has a stability exceeding that of known lyophilized caspofungin-containing compositions which employ sucrose and mannitol and have a $T_g(c)$ in a range of from about 40° C. to about 45° C.

Embodiments, aspects and features of the present invention are either further described in or will be apparent from the ensuing description, examples, and appended claims.

DETAILED DESCRIPTION OF THE INVENTION

A first embodiment of the present invention (alternatively referred to herein as "Embodiment E1") is a lyophilized composition as originally described (i.e., as described in the Summary of the Invention) wherein the one or more non-reducing sugars is selected from the group consisting of trehalose, sucrose, raffinose, sorbitol and combinations thereof. Suitable combinations include any two of the sugars (e.g., trehalose and sucrose), any three of the sugars (e.g., trehalose, sucrose, and sorbitol), or all four of the sugars. In an aspect of this embodiment, the one or more non-reducing sugars is trehalose or a mixture of trehalose with any one of sucrose, raffinose and sorbitol. In a feature of this aspect, the non-reducing sugar is trehalose or a major amount of trehalose (i.e., trehalose is more than 50 wt. % of the mixture) with any one of sucrose, raffinose and sorbitol. In another feature of this aspect, the non-reducing sugar is trehalose or is a combination of at least about 80 wt. % trehalose with any one of sucrose, raffinose and sorbitol.

A second embodiment of the present invention (Embodiment E2) is a lyophilized composition as originally described wherein trehalose is the one or more non-reducing sugars; i.e., there is one non-reducing sugar present in the composition and that sugar is trehalose. This is alternatively and more simply expressed herein as "trehalose is the non-reducing sugar".

A third embodiment of the present invention (Embodiment E3) is a lyophilized composition as originally described or as set forth in either Embodiment E1 or E2 wherein the moisture content of the composition is about 0.5 wt. % or less.

A fourth embodiment of the present invention (Embodiment E4) is a lyophilized composition as originally described or as set forth in either Embodiment E1 or E2 wherein the moisture content of the composition is about 0.3 wt. % or less.

A fifth embodiment of the present invention (Embodiment E5) is a lyophilized composition as originally described or as set forth in any one of the foregoing embodiments wherein the glass transition temperature $T_g(c)$ of the composition is at least about 90° C.

A sixth embodiment of the present invention (Embodiment E6) is a lyophilized composition as originally described or as set forth in any one of the foregoing embodiments wherein the glass transition temperature $T_g(c)$ of the composition is in a range of from about 90° C. to about 125° C.

A seventh embodiment of the present invention (Embodiment E7) is a lyophilized composition as originally described or as set forth in any one of the foregoing embodiments wherein the non-reducing sugar-to-caspofungin weight ratio of the composition is in a range of from about 2:1 to about 8:1.

An eighth embodiment of the present invention (Embodiment E8) is a lyophilized composition as originally described or as set forth in any one of the foregoing embodiments wherein the non-reducing sugar-to-caspofungin weight ratio of the composition is in a range of from about 2:1 to about 6:1.

A ninth embodiment of the present invention (Embodiment E9) is a lyophilized composition as originally described wherein trehalose is the non-reducing sugar, the moisture content of the composition is about 0.5 wt. % or less, the glass transition temperature $T_g(c)$ of the composition is at least about 90° C., and the trehalose-to-caspofungin weight ratio is in a range of from about 2:1 to about 8:1. In an aspect of this embodiment, the glass transition temperature $T_g(c)$ is in a range of from about 90° C. to about 125° C.

A tenth embodiment of the present invention (Embodiment E10) is a lyophilized composition as originally described wherein trehalose is the non-reducing sugar, the moisture content is about 0.3 wt. % or less, the glass transition temperature $T_g(c)$ is at least about 90° C., and the trehalose-to-caspofungin weight ratio is in a range of from about 2:1 to about 6:1. In an aspect of this embodiment, the glass transition temperature $T_g(c)$ is in a range of from about 90° C. to about 125° C.

An eleventh embodiment of the present invention (Embodiment E11) is a lyophilized composition as originally described which is prepared by lyophilizing an aqueous solution comprising the caspofungin or its salt, the acetate buffer, and the one or more non-reducing sugars, wherein in the solution:

(A) the caspofungin or its salt has a concentration in a range of from about 5 mg/mL to about 200 mg/mL;

(B) the one or more non-reducing sugars has a concentration ratio on a mg/mL basis with respect to caspofungin in a range of from about 2:1 to about 10:1; and (C) the acetate buffer has a concentration in a range of from about 12.5 mM to about 200 mM.

Aspects of Embodiment E11 include the lyophilized composition as just described in Embodiment E11, wherein:

(A1) the one or more non-reducing sugars is a sugar selected from the group consisting of trehalose, sucrose, raffinose, sorbitol and combinations thereof.

(A2) trehalose is the non-reducing sugar.

(A3) the moisture content of the composition is about 0.5 wt. % or less.

(A4) the moisture content of the composition is about 0.3 wt. % or less.

(A5) the glass transition temperature $T_g(c)$ of the composition is at least about 90° C.

(A6) the glass transition temperature $T_g(c)$ of the composition is in a range of from about 90° C. to about 125° C.

(A7) the non-reducing sugar(s)-to-caspofungin weight ratio of the composition is in a range of from about 2:1 to about 8:1.

(A8) the non-reducing sugar(s)-to-caspofungin weight ratio of the composition is in a range of from about 2:1 to about 6:1.

(A9) trehalose is the non-reducing sugar, the moisture content of the composition is about 0.5 wt. % or less, and the glass transition temperature $T_g(c)$ is at least about 90° C.

(A10) the composition is the same as set forth in A9, except that the moisture content is about 0.3 wt. % or less.

(A11) trehalose is the non-reducing sugar, the moisture content is of about 0.5 wt. % or less, the glass transition temperature $T_g(c)$ is at least about 90° C., and the trehalose-to-caspofungin weight ratio is in a range of from about 2:1 to about 8:1.

(A12) trehalose is the non-reducing sugar, the moisture content is about 0.3 wt. % or less, the glass transition temperature $T_g(c)$ is at least about 90° C., and the trehalose-to-caspofungin weight ratio is in a range of from about 2:1 to about 6:1.

(A13) the composition is the same as set forth in A11 except that the glass transition temperature $T_g(c)$ is in a range of from about 90° C. to about 125° C.

(A14) the composition is the same as set forth in A12 except that the glass transition temperature $T_g(c)$ is in a range of from about 90° C. to about 125° C.

A twelfth embodiment of the present invention (Embodiment E12) is a lyophilized composition as set forth in Embodiment E11, wherein in the aqueous solution from which the lyophilized composition is prepared:

(A) the concentration of caspofungin or its salt is in a range of from about 30 mg/mL to about 50 mg/mL;

(B) the concentration ratio of the non-reducing sugar(s) to caspofungin is in a range of from about 4:1 to about 8:1; and (C) the concentration of the acetate buffer is in a range of from about 20 mM to about 60 mM.

A thirteenth embodiment of the present invention (Embodiment E13) is a lyophilized composition as set forth in Embodiment E12, wherein trehalose is the non-reducing sugar, the moisture content of the composition is about 0.5 wt. % or less (e.g., about 0.3 wt. % or less), and the glass transition temperature $T_g(c)$ of the composition is at least about 90° C. (e.g., in a range of from about 90° C. to about 125° C.).

A fourteenth embodiment of the present invention (Embodiment E14) is a lyophilized composition as set forth in Embodiment E13, wherein in the aqueous solution from which the lyophilized composition is prepared:

(A) the concentration of caspofungin or its salt is in a range of from about 30 mg/mL to about 50 mg/mL;

(B) the concentration of trehalose is in a range of from about 180 mg/mL to about 300 mg/mL (i.e., a trehalose to caspofungin concentration ratio of about 6:1); and (C) the acetate buffer has a concentration in a range of from about 20 mM to about 60 mM.

A fifteenth embodiment of the present invention (Embodiment E15) is a lyophilized composition as originally described or as set forth in any of the foregoing embodiments or aspects or features thereof, wherein the composition is substantially free of reducing sugars. Reducing sugars can have a detrimental effect on the stability of the lyophilized compositions of the present invention (see below), and thus the compositions preferably contain little or no reducing sugar. The term "substantially free" in this context means that no reducing sugar is included as a component in the preparation of the lyophilized composition and/or that essentially no reducing sugar is present in the lyophilized composition.

An "effective amount" of caspofungin in the lyophilized composition is an amount of caspofungin (on a free base basis) that upon reconstitution of the lyophilized composition can be employed (e.g., via parenteral administration) in a therapeutically or prophylactically effective amount to treat or prevent a fungal infection or the like.

The term "pharmaceutically acceptable salt" refers to a salt which is not biologically or otherwise undesirable (e.g., is neither toxic nor otherwise deleterious to the recipient thereof). The caspofungin salt can suitably be a mono-, di-, or tri-acid salt. The salts are suitably prepared by treating the free base with a suitable organic or inorganic acid. Suitable salts include acid addition salts such as the salts formed by treating the free base with hydrochloric acid, hydrobromic acid, phosphoric acid, sulfuric acid, maleic acid, critic acid, or acetic acid.

The term "non-reducing sugar" refers to a carbohydrate that does not reduce alkaline solutions of copper. Non-reducing sugars do not participate in the Maillard reaction with compounds containing primary amines (e.g., amino acids). The reducing or non-reducing nature of a sugar can be determined by the Fehling's test, which monitors the reduction of Cu++ to Cu+, with concomitant oxidation of the sugar. Non-reducing sugars do not react in the Fehling's test (i.e., they do not lead to the formation of cuprous oxide). Exemplary non-reducing sugars suitable for use in the present invention include trehalose, sucrose, raffinose, and sorbitol.

A "reducing sugar" refers to a carbohydrate that does reduce alkaline solutions of copper (e.g., does react in the Fehling's test) and does participate in the Maillard reaction with compounds containing primary amines.

The glass transition temperatures referred to herein (e.g., $T_g(s)$ and $T_g(c)$) are the transition temperatures determined using differential scanning calorimetry (DSC). DSC measures the change in heat capacity between the glassy and rubbery states and is typically indicated by a change in baseline in a DSC thermogram.

The glass transition temperature $T_g(c)$ of the lyophilized composition of the present invention will typically decrease as the amount of moisture in the composition increases. Furthermore, even in cases where the lyophilized composition can tolerate a relatively large amount of moisture and still have a suitable $T_g(c)$, the presence of a relatively large amount of moisture is often deleterious for other reasons. For example, the moisture can be a source of chemical degradation of the active ingredient by, for example, hydrolysis. Accordingly, the lyophilized composition of the present invention is characterized by having a low moisture content. More particularly, for the purposes of this invention, if (i) the amount of moisture in the composition is about 0.8 wt. % or less and (ii) the $T_g(c)$ of the lyophilized composition is at least about 55° C., then the composition is deemed to have a low moisture content and to be a composition of the present invention. Both (i) and (ii) must be satisfied for the composition to be a composition of the present invention. Thus, if a lyophilized composition has a moisture content of less than about 0.8 wt. % but its $T_g(c)$ is below about 55° C., the composition is not a composition of the present invention. Furthermore, if a lyophilized composition has a $T_g(c)$ above about 55° C. but its moisture content is more than 0.8 wt. %, the composition is not considered as having a low moisture content and is not a composition of the present invention. The lyophilized composition of the invention typically has a moisture content of less than about 0.5 wt. % and a $T_g(c)$ above about 55° C., and preferably has a moisture content of less than about 0.5 wt. % and a $T_g(c)$ above about 90° C.

$T_g(s)$, the glass transition temperature of the one or more non-reducing sugars employed in the lyophilized anti-fungal composition of the invention is the glass transition temperature of the sugar(s) after lyophilization of the non-reducing sugar(s) in the same manner as the anti-fungal composition is lyophilized, wherein the lyophilization generates an amorphous form of the non-reducing sugar(s). The $T_g(s)$ value of the one or more non-reducing sugars used in the present invention is at least about 90° C. and is typically in a range of from about 90° C. to about 125° C.

When more than one non-reducing sugar is employed, it is the $T_g(s)$ value of the the sugars together in a mixture (after lyophilization) that must be at least about 90° C. A non-reducing sugar whose glass transition temperature is below 90° C. can be included in the composition, provided that the $T_g(s)$ of all of the non-reducing sugars together (after lyophilization) is about 90° C. or higher. Typically, however, each of the non-reducing sugars employed in the lyophilized composition has an individual glass transition temperature of at least about 90° C.

The moisture content of the lyophilized composition is determined by the Karl Fisher coulometry method, wherein the residual water is extracted from the composition using methanol or some other suitable extraction agent. The water present in the methanol or other reagent is then titrated with a Karl Fischer solution that reacts with the water to form colorless hydrogen iodide. When all of the water has been consumed, free iodine, which has color, appears, thereby indicating an end point before which the conductivity of the solution will have changed. The moisture content can then be determined from a measurement of the amount of HI formed during the titration.

The term "about", when modifying the quantity of a substance or composition, or the value of a physical property (e.g., moisture content, $T_g(c)$, $T_g(s)$, or the like) of a substance or composition, or the value of a parameter characterizing a process, or the like refers to variation in the numerical quantity that can occur, for example, through typical measuring and handling procedures employed in the preparation, characterization, and use of the lyophilized compositions of the invention; for making concentrates or use solutions in the real world; through inadvertent error in these procedures; through differences in the manufacture, source, or purity of the ingredients employed to make or use the compositions or carry out the procedures; and the like. In one embodiment, the term "about" means the reported numerical value±10% thereof. In an aspect of this embodiment, the term "about" means the reported numerical value±5% thereof.

An "effective amount" of an acetate buffer is an amount of the buffer that can provide, with suitable adjustment as needed by addition of base (e.g., a hydroxide such as NaOH), a pH in the indicated range in the aqueous solution from which the lyophilized composition of the invention is prepared (i.e., in the pre-lyophilization solution).

Unless expressly stated to the contrary, a reference to pH herein means the pH at ambient temperature; i.e., at a temperature in a range of from about 20° C. to about 25° C.

The lyophilized compositions of the present invention are not limited to the active ingredient (i.e., caspofungin) or its salt, the acetate buffer and the non-reducing sugar(s). The composition can include other components such as (i) a minor amount of a bulking agent (e.g., a polyol) in addition to the non-reducing sugar(s) or (ii) an anti-oxidant such as BHT, BHA, alpha-tocopherol, or ascorbic acid. If employed, the bulking agent is typically present in an amount of less than about 10 wt. %, preferably less than about 5 wt. %, with respect to the non-reducing sugar(s).

The present invention also includes a process for preparing a lyophilized anti-fungal composition with a moisture content of less than about 0.8 wt. % (alternatively referred to herein as "Process P1"), which comprises (A) preparing an aqueous solution with a pH in a range of from about 5 to about 7 and comprising an effective amount of caspofungin or a pharmaceutically acceptable salt thereof, one or more non-reducing sugars having a glass transition temperature $T_g(s)$ of at least about 90° C., and an acetate buffer, wherein the concentration ratio, on a weight per unit volume basis, of the one or more non-reducing sugars to caspofungin is in a range of from about 1.1:1 to about 10:1; and (B) freeze-drying the aqueous solution to provide the lyophilized anti-fungal composition.

A first embodiment of Process P1 (alternatively referred to herein as "Embodiment P1-E1") is the process as originally described, wherein Step A further comprises:

(a1) dissolving the one or more non-reducing sugars in water;

(a2) adding acetic acid and then adjusting the pH to be in a range of from about 4.5 to about 5.5 by addition of base;

(a3) adding caspofungin or its salt and adjusting the pH to a value in a range of from about 5 to about 7 (e.g., about 6) by addition of more base; and (a4) optionally filtering the resulting aqueous solution.

When more than one non-reducing sugar is employed in sub-step a1 of Step A in the Process P1, the sugars can be dissolved in any convenient way. For example, the sugars can be mixed together and the dry mixture dissolved in water to provide the solution employed in sub-step a2, or alternatively the sugars can be dissolved individually in separate portions of water to provide separate aqueous sub-solutions and the separate sub-solutions added together and optionally diluted if necessary to give the solution employed in sub-step a2, or alternatively the sugars can be added separately to the same portion of water and dissolved therein and optionally diluted if necessary to provide the solution employed in sub-step a2. When added separately, the individual non-reducing sugars can be added concurrently or at different times in any order.

A second embodiment of Process P1 (Embodiment P1-E2) is the process as originally described or as set forth in Embodiment P1-E1, wherein in the aqueous solution resulting from Step A the caspofungin or its salt has a concentration in a range of from about 5 mg/mL to about 200 mg/mL, and the concentration ratio of the non-reducing sugar(s) to caspofungin is in a range of from about 2:1 to about 10:1.

A third embodiment of Process P1 (Embodiment P1-E3) is the process as originally described or as set forth in Embodiment P1-E1, wherein in the aqueous solution resulting from Step A the caspofungin or its salt has a concentration in a range of from about 30 mg/mL to about 50 mg/mL, and the concentration ratio of the non-reducing sugar(s) to caspofungin is in a range of from about 4:1 to about 8:1.

A fourth embodiment of Process P1 (Embodiment P1-E4) is the process as originally described or as set forth in any one of Embodiments P1-E1 to P1-E3, wherein the one or more non-reducing sugars is selected from the group consisting of trehalose, sucrose, raffinose, sorbitol and mixtures thereof.

A fifth embodiment of Process P1 (Embodiment P1-E5) is the process as originally described or as set forth in any one of Embodiments P1-E1 to P1-E3, wherein trehalose is the non-reducing sugar.

A sixth embodiment of Process P1 (Embodiment P1-E6) is the process as originally described or as set forth in any one of the foregoing embodiments of P1, wherein the moisture content of the lyophilized composition is about 0.5 wt. % or less.

A seventh embodiment of Process P1 (Embodiment P1-E7) is the process as originally described or as set forth in any one of the foregoing embodiments of P1, wherein the moisture content of the lyophilized composition is about 0.3 wt. % or less.

An eighth embodiment of Process P1 (Embodiment P1-E8) is the process as originally described or as set forth in any one of the foregoing embodiments of P1, wherein the lyophilized composition has a glass transition temperature $T_g(c)$ of at least about 90° C. (e.g., in a range of from about 90° C. to about 125° C.).

The present invention also includes a lyophilized anti-fungal composition prepared by the process P1 as originally described or as set forth in any one of the foregoing embodiments of P1.

The freeze-drying (i.e, lyophilizing) of the aqueous solution resulting from Step A of Process P1 involves first cooling the solution to a temperature at or below the freezing point of the solution (i.e., below its glass transition temperature if the solution forms a glass upon cooling and below its eutectic point if the frozen solution is crystalline). The frozen solution is then typically subjected to a primary drying step in which the temperature is gradually raised under vacuum in a drying chamber to remove most of the water, and then to a secondary drying step typically at a higher temperature than employed in the primary drying step to remove the residual moisture in the lyophilized composition. The freeze drying step typically requires 48 hours or more to complete. The lyophilized composition is then appropriately sealed and stored (e.g., in stoppered vials) for later use. Tang et al., *Pharmaceutical Research* 2004, vol. 21, pp. 191-200 describes the scientific principles pertaining to freeze drying and guidelines for designing suitable freeze drying processes. Further description of freeze drying is found in *Remington—The Science and Practice of Pharmacy,* 2006, 21$^{st}$ edition, Lippincott Williams & Wilkins, pp. 828-831.

The lyophilized compositions of the present invention are characterized by having good chemical and storage stability at temperatures up to and including room temperature. Caspofungin has two main degradation products. The first is formed via hydrolysis in the pre-lyophilization solution, and the second is formed in the lyophilized composition as a result of intramolecular rearrangement. It has been found that the lyophilized compositions of the present invention exhibit reduced growth of the second degradate during storage compared to analogous known compositions with the same or similar moisture content.

The lyophilized compositions of the present invention are reconstituted for use in preventing or treating fungal infections. The present invention accordingly includes a method of preparing an anti-fungal liquid formulation for parenteral administration (alternatively referred to herein as "Method M1"), which comprises reconstituting (i) the lyophilized anti-fungal composition as originally described in the Summary of the Invention or as set forth in any one of Embodiments E1 to E15 or in any aspects or features thereof or (ii) the lyophilized anti-fungal composition resulting from Process P1 as originally described or as set forth in any one Embodiments P1-E1 to P1-E8 with a parenterally acceptable solvent to form an anti-fungal solution concentrate and then mixing the concentrate with a diluent comprising water to provide the formulation.

A first embodiment of Method M1 (alternatively referred to herein as "Embodiment M1-E1") is the Method M1 as originally described, wherein the parenterally acceptable solvent comprises water.

A second embodiment of Method M1 (Embodiment M1-E2) is the Method M1 as originally described, wherein the parenterally acceptable solvent is selected from the group consisting of 0.9% Sodium Chloride Injection, Sterile Water for Injection, Bacteriostatic Water for Injection with methylparaben and propylparaben, and Bacteriostatic Water for Injection with 0.9% benzyl alcohol.

A third embodiment of Method M1 (Embodiment M1-E3) is the Method M1 as originally described or as set forth in either Embodiment M1-E1 or M1-E2, wherein the diluent is 0.9%, 0.45% or 0.225% Sodium Chloride Injection or Lactated Ringer's Injection.

A fourth embodiment of Method M1 (Embodiment M1-E4) is the Method M1 as originally described or as set forth in any of the foregoing embodiments of M1, wherein the concentrate contains from about 5 mg/mL to about 8 mg/mL of caspofungin, and the liquid formulation resulting from dilution of the concentrate contains from about 0.2 mg/mL to about 0.5 mg/mL of caspofungin.

The present invention further includes an anti-fungal liquid dosage formulation for parenteral administration prepared by the Method M1 as originally described or as set forth in any one of the foregoing embodiments of M1.

The present invention still further includes a method for the treatment or prophylaxis of a fungal infection which comprises parenterally administering to a subject in need thereof an anti-fungal liquid formulation prepared by the Method M1 as originally described or as described in any one of the foregoing embodiments of Method M1.

The present invention also includes an anti-fungal liquid dosage formulation prepared by the Method M1 as originally described or as described in any one of the foregoing embodiments of Method M1 (i) for use in, (ii) for use as a medicament for, or (iii) for use in the preparation of a medicament for the treatment or prophylaxis of a fungal infection.

The present invention still further includes a kit comprising a first container having the (i) the lyophilized anti-fungal composition as originally described in the Summary of the Invention or as set forth in any one of Embodiments E1 to E15 or in any aspects or features thereof or (ii) the lyophilized anti-fungal composition resulting from Process P1 as originally described or as set forth in any one Embodiments P1-E1 to P1-E8 and a second container having a parenterally acceptable solvent for reconstitution thereof. The kit can include other components such as vials, stirrers, lids, and instructions for reconstitution, mixing, storage and/or use.

As used herein, parenteral administration includes but is not limited to administration of the formulation by subcutaneous injection or via intravenous or intramuscular injection or infusion techniques. The anti-fungal liquid dosage formulation of the invention is typically administered by intravenous infusion.

A "parenterally acceptable solvent" is a solvent which is not biologically or otherwise undesirable (e.g., does not typically produce an unintended allergic reaction or other adverse event) during or following parenteral administration.

The regimens utilizing a dosage formulation of the present invention for parenteral administration are selected in accordance with a variety of factors including type of species being administered to (i.e., animal, preferably mammal, and most preferably human); the age, weight, sex and medical condition of the patient; the severity of the condition to be treated; and the renal and hepatic function of the patient. A veterinarian or physician of ordinary skill can readily determine and prescribe a dose suitable for preventing or treating the anti-fungal infection. Further description on the dosage and administration of caspofungin to humans is provided in the entry for Intravenous Infusion CANCIDAS in the 2007 edition of the *Physician's Desk Reference*.

The following examples serve only to illustrate the invention and its practice. The examples are not to be construed as limitations on the scope or spirit of the invention.

The high performance liquid chromatography (HPLC) analysis referred to in Example 3 below was conducted using: column=Waters Symmetry C18 (5 μm particle size, 250×4.6 mm); column temperature=ambient; detection=UV absorbance at 220 nm; autosampler=temperature controlled at approximately 5° C.; diluent=acetonitrile; sodium acetate buffer: 1:4; mobile phase A: 0.1% perchloric acid, 0.075% NaCl; mobile phase B: acetonitrile; program:

| Time (min) | % A | % B | Flow rate (mL/min) |
|---|---|---|---|
| 0 | 65.5 | 34.5 | 1.0 |
| 14.5 | 65.5 | 34.5 | 1.0 |
| 35 | 50 | 50 | 1.0 |
| 45 | 35 | 65 | 1.0 |
| 50 | 20 | 80 | 1.0 |
| 52 | 20 | 80 | 1.0 |
| 53 | 65.5 | 34.5 | 1.0 |
| 53.5 | 65.5 | 34.5 | 1.0 |
| 54 | 65.5 | 34.5 | 1.5 |
| 63 | 65.5 | 34.5 | 1.5 |
| 63.5 | 65.5 | 34.5 | 1.0 |
| 66 | 65.5 | 34.5 | 1.0 |

The retention time for caspofungin is 20.3 minutes.

EXAMPLE 1

Preparation of Lyophilized Caspofungin Diacetate Composition

Trehalose (11.99 g) was dissolved in 30 mL of water, followed by the addition of glacial acetic acid (75 μL; density=1.049 g/mL) to provide a solution with a pH of about 3. The solution pH was adjusted to about 5.1 by the addition of 1N NaOH, after which caspofungin diacetate (2.23 g=2.00 g of free base) was added and the mixture gently stirred and shaken to dissolve the caspofungin without foaming. The pH of the solution was then adjusted to 6.0 by addition of 1N NaOH. Water was then added to bring the volume of the solution to 50 mL and the resulting solution was filtered through 0.22 μm filter units. This pre-lyophilization solution had the following composition:

caspofungin diacetate (free base equivalent)=40.0 mg/mL trehalose=240.0 mg/mL glacial acetic acid=1.5 mg/mL NaOH=sufficient to provide pH=6.0 water for injection=q.s. 1.00 mL

Aliquots of 0.5 mL of the solution were then placed in 3 mL lyophilization vials and the vials partially stoppered with 13 mm bromobutyl lyo stoppers (4405/50 gray) (available from West Pharmaceutical Services) which had been dried overnight at 110° C.

The vials were then lyophilized using a VirTis Genesis lyophilizer. The vials were placed in lyophilization trays and the trays loaded onto the lyophilizer shelves. The cycle of steps employed to obtain lyophilized compositions was as follows:

| Lyophilization Cycle Step |
| --- |
| 1. Cool to −40° C. @ 0.2° C./min |
| 2. Hold at −40° C. for 120 min |
| 3. Apply 80 mTorr vacuum |
| 4. Ramp to −20° C. @ 0.1° C./min |
| 5. Hold at −20° C. for 3000 min |
| 6. Ramp to −15° C. @ 0.1° C./min |
| 7. Hold at −15° C. for 900 min |
| 8. Ramp to −10° C. @ 0.1° C./min |
| 9. Hold at −10° C. for 400 min |
| 10. Ramp to −5° C. @ 0.1° C./min |
| 11. Hold at −5° C. for 400 min |
| 12. Ramp to +15° C. @ 0.1° C./min |
| 13. Hold at +15° C. for 720 min |
| 14. Ramp to +25° C. @ 1° C./min |
| 15. Hold at +25° C. for 240 min |

The lyophilized compositions were stored in the lyophilized state at 5° C., 25° C. and 30° C., and then tested after 1, 2, 4 and 6 months for stability in the manner described in Example 3.

Glass Transition Temperatures.

The $T_g(c)$ of the lyophilized composition was determined using a DSC Q2000 (TA Instruments) under a stream of nitrogen gas at 50 mL/minute as the purge gas. Several samples of the lyophilized composition (each about 5 mg) were prepared in a nitrogen purged glove box, and each was loaded into an aluminum DSC pan and hermetically sealed. The pans along with an empty pan as control were run in the DSC. The pans were first equilibrated at 25° C., then modulated at ±0.5° C. every 60 seconds, and then the temperature was raised at a rate of 2.5° C. per minute to a final temperature of 140° C. The samples was determined to have a $T_g(c)$ of 97±2° C.

Several samples of trehalose were lyophilized in the same manner as set forth above for the caspofungin diacetate composition. The glass transition temperature Tg(s) of each of the lyophilized trehalose samples was determined using the instrument and procedure employed to determine Tg(c) described in the preceding paragraph. The average Tg(s) of the samples was 118±2° C.

Moisture Content.

The moisture content of the lyophilized composition was determined via Karl Fischer coulometry (extraction agent—methanol:formamide in 1:1 ratio by volume) to be 0.3±0.2 wt. % (n=3).

EXAMPLE 2

Preparation of Lyophilized Compositions

The lyophilized compositions 2-1 to 2-10 listed in Table 2 below were prepared in a manner similar to that set forth for the lyophilized composition of Example 1, except that the secondary drying in the lyophilization cycle was performed at 15° C. instead of 25° C.: The $T_g(c)$ and moisture content of the lyophilized compositions were determined in the manner described in Example 1. Table 2 also lists the corresponding values for the composition prepared in Example 1 and for the marketed product CANCIDAS.

TABLE 2

| | Lyophilized Compositions[1,2] | | | | |
| --- | --- | --- | --- | --- | --- |
| Example No. | CPFGN free base (mg/mL) | SUG (mg/mL) | SUG:CPFGN weight ratio | Tg (c) (° C.) | Moisture content (wt. %) |
| 2-1 | 40.0 | MAN = 20.0<br>SUC = 30.0 | 1.25 | 42 | ~0.5 |
| 2-2 | 40.0 | MAN = 20.0<br>SUC = 30.0 | 1.25 | 40-45 | 0.15 |
| 2-3 | 37.8 | MAN = 20.0<br>SUC = 30.0 | 1.32 | n.m. | 0.57 |
| 2-4 | 37.8 | TRE = 50.0 | 1.32 | n.m. | 0.50 |
| 2-5 | 37.8 | TRE = 30.0<br>LAC = 20.0 | 1.32 | n.m. | 0.79 |
| 2-6 | 37.8 | TRE = 20.0<br>LAC = 30.0 | 1.32 | n.m. | 0.62 |
| 2-7 | 37.8 | LAC = 50.0 | 1.32 | n.m. | 0.61 |
| 2-8 | 40.0 | TRE = 20.0 | 0.5 | n.m.[3] | 0.56 |
| 2-9 | 40.0 | TRE = 40.0 | 1.0 | n.m.[3] | 0.52 |
| 2-10 | 40.0 | TRE = 80.0 | 2.0 | 93 | 0.46 |
| 1 | 40.0 | TRE = 240.0 | 6.0 | 97 | 0.3 |
| MP | 42.0 | MAN = 20.0<br>SUC = 30.0 | 1.20 | 40-45 | ~0.5 |

[1]CPFGN = caspofungin; LAC = lactose; MAN = mannitol; n.m. = not measured; MP = marketed product CANCIDAS; SUC = sucrose; SUG = sugar(s); TRE = trehalose.
[2]The pre-lyophilization solution for each of these compositions had a pH of 6.0, contained 1.5 mg/mL of glacial acetic acid, NaOH = q.s. pH 6, and water for injection = q.s. 1 mL.
[3]The Tg(c) values for these samples were not determined, but it is believed these compositions have Tg(c)'s of about 90.

Immediately following preparation, each of the the lyophilized compositions was tested for stability in the manner described in Example 3. The lyophilized compositions in Table 2 differ in their moisture content. As noted earlier, moisture can be a source of chemical degradation of caspofungin by, for example, hydrolysis. However, the moisture content in all of these compositions is believed too low to be a significant factor in the interpretation of the stability results reported in Example 3; i.e., the trends in stability observed in Example 3 are primarily due to the choice and relative amounts of the sugars employed in the compositions and not to any differences in moisture content.

EXAMPLE 3

Stability Tests

A. The stabilities of compositions 2-3, 2-4, 2-5, 2-6 and 2-7 were compared by placing samples of each composition at each of several temperature stations and monitoring their stability after 2 weeks, 4 weeks and 8 weeks. Three vials of each of these compositions were placed for each time point at each of the following stations: 5° C., 25° C. at 65% relative humidity (RH) and 40° C. at 75% RH. (Note: RH is not considered to be a critical parameter since the lyophilized compositions are in glass vials sealed with stoppers and caps so that no moisture exchange should occur.) The sample vials were tested for stability after the first 2 weeks by determining the amount of caspofungin in the samples using HPLC. Examples 2-3, 2-4 and 2-7 were then selected for testing to and comparison at 4 weeks, and subsequently Examples 2-3 and 2-4 were selected for testing to and comparison at 8 weeks. The selective results obtained at 8 weeks were consistent with the 2-week and 4-week results, which are shown in Table 3-A below.

TABLE 3-A

| Ex. No. | Temp (° C.) | Timepoint (wks) | CPFGN assay (%) |
|---|---|---|---|
| 2-3 | 40 | 2 | 54.2 |
| 2-3 | 40 | 4 | 39.0 |
| 2-4 | 40 | 2 | 94.5 |
| 2-4 | 40 | 4 | 90.5 |
| 2-5 | 40 | 2 | 83.3 |
| 2-6 | 40 | 2 | 80.5 |
| 2-7 | 40 | 2 | 78.2 |
| 2-7 | 40 | 4 | 57.0 |

The data in Table 3-A demonstrate that the lyophilized composition of Example 2-4 is the most stable of the compositions tested in terms of loss of caspofungin. The data also indicate that formulations containing trehalose (2-4, 2-5, 2-6) were more stable than the non-trehalose-containing formulations (2-3 and 2-7). While not wishing to be bound by any particular theory, it is believed that the lower stability observed for the lactose-containing formulations is due to the Maillard reaction that occurs between reducing sugars, such as lactose, and molecules, such as caspofungin, containing a nucleophilic amino group.

B. The stabilities of the compositions 2-1, 2-8, 2-9 and 2-10 were compared by placing samples of each composition at each of several temperature stations and monitoring their stability at 4-week intervals for 8 weeks. More particularly, 3 vials of each of these compositions were placed for each time point at each of the following stations: 5° C., 25° C. at 65% RH, 30° C. at 60% RH, and 40° C. at 75% RH. The sample vials were tested for stability by determining the amount of caspofungin and the casponfungin degradate that forms in the lyophilized cake over time (determined as wt. % of caspofungin) in the samples using HPLC. The results are shown in Table 3-B below.

TABLE 3-B

| Ex. No. | Temp (° C.) | Timepoint (wks) | CPFGN assay (%) | Degradate (wt. % of active) |
|---|---|---|---|---|
| 2-1 | 30 | 8* | 75.1 | 3.2 |
|  | 40 | 8* | 21.5# | 0.5# |
| 2-8 | 30 | 8* | 81.0 | 2.3 |
|  | 40 | 8* | 65.3 | 4.3 |
| 2-9 | 30 | 8* | 83.9 | 1.8 |
|  | 40 | 8* | 75.7 | 3.9 |
| 2-10 | 30 | 8* | 83.5 | 1.6 |
|  | 40 | 8* | 79.9 | 3.2 |

*The stoppers were not properly dried and the moisture content was measured to be ~2.0% after 1 month
No mass balance The results in Table 3-B show that the stability of the trehalose-containing lyophilized compositions is superior to that of the lyophilized composition containing no trehalose (i.e., Ex. No. 2-1 containing sucrose and mannitol) and that the stability of the trehalose-containing compositions increases with increasing concentration of trehalose. More particularly, as the ratio of trehalose to caspofungin free base increased from 0.5 to 1.0 to 2.0, the generation of degradate decreased from 2.3% to 1.8% to 1.6%, respectively, at 30° C. after 8 weeks. A similar trend was observed at 40° C.

C. The stabilities of the compositions of Examples 1 and 2-2 were compared by placing samples of each composition at each of several temperature stations and monitoring their stability after 4-week, 8-week, 16-week, 24-week and 72-week (at 30° C. for only Example 1 formulation) time points. More particularly, 3 vials of each of the two compositions were placed for each time point at each of the following stations: 5° C., 25° C. at 65% RH, 30° C. at 60% RH, and 40° C. at 75% RH. The sample vials were tested for stability for up to 24 weeks by determining the amount of caspofungin and the casponfungin degradate that forms in the lyophilized composition over time (calculated as wt. % of active) in the samples using HPLC. The results are shown in Table 3-C below. Table 3-C also contains historical data based on two different lots of the marketed product MP (CANCIDAS™), wherein each lot included lyophilized product containing 35 mg, 50 mg, and 75 mg of caspofungin.

TABLE 3-C

| Ex. No. | $T_g(c)^1$ (° C.) | Temp (° C.) | Timepoint (wks) | CPFGN assay (%) | Key Degradate (% of CPFGN) |
|---|---|---|---|---|---|
| MP | 40-45 | 30 | 24 |  | 2.1 |
|  |  |  | 52 | 89.24 | 4.7 |
| 2-2 | 40-45 | 30 | 24 | 101.3² | 0.8 |
| 2-2 |  | 40 | 16 | 77.0 | 6.0 |
|  |  |  | 24 | n.a.³ | n.a. |
| 1 | 97 | 30 | 8 | 98.5 | 0.7 |
|  |  |  | 16 | 97.9 | 0.8 |
|  |  |  | 24 | 95.5 | 1.2 |
|  |  |  | 72 | 93.4 | 1.7 |
| 1 |  | 40 | 24 | 88.0 | 1.9 |

¹Tg(c) values are from TABLE 2.
²Although >100%, the value was within fill and analytical variances.
³n.a. = not assayed, due to severe browning of the sample which accordingly was not deemed fit for analysis.

The results in Table 3-C show that Example 1 exhibits a long-term thermal stability superior to that observed for the marketed product and for Example 2-2. More particularly, the level of degradate generated in Example 1 after 24 weeks and 72 weeks at 30° C. is markedly less than the degradate levels seen in MP at 24 weeks and 52 weeks, respectively. Example 1 has a degradate level higher than that of Example 2-2 at 30° C., but Example 1 is much more stable than 2-2 at 40° C.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A lyophilized anti-fungal composition which comprises:
   (A) caspofungin, or a pharmaceutically acceptable salt thereof, in an effective amount;
   (B) one or more non-reducing sugars having a glass transition temperature $T_g(s)$ of at least about 90° C.; and
   (C) an acetate buffer in an amount effective to provide a pH in a range of from about 5 to about 7;
   wherein:
   the weight ratio of the one or more non-reducing sugars to caspofungin is in a range of from about 1.1:1 to about 10:1;
   trehalose is the non-reducing sugar;
   the composition has a moisture content of about 0.8 wt. % or less; and
   the composition has a glass transition temperature $T_g(c)$ of at least about 55° C.

2. The lyophilized composition according to claim 1, wherein the moisture content of the composition is about 0.5 wt. % or less and the glass transition temperature $T_g(c)$ of the composition is at least about 90° C.

3. The lyophilized composition according to claim 1, which is prepared by lyophilizing an aqueous solution comprising the caspofungin or its salt, the acetate buffer, and the one or more non-reducing sugars, wherein in the solution:

(A) the caspofungin or its salt has a concentration in a range of from about 5 mg/mL to about 200 mg/mL;
(B) the one or more non-reducing sugars has a concentration ratio on a mg/mL basis with respect to caspofungin in a range of from about 2:1 to about 10:1; and
(C) the acetate buffer has a concentration in a range of from about 12.5 mM to about 200 mM.

4. The lyophilized composition according to claim 3, wherein trehalose is the non-reducing sugar, the moisture content of the lyophilized composition is about 0.5 wt. % or less, and the glass transition temperature $T_g(c)$ of the lyophilized composition is at least about 90° C.

5. The lyophilized composition according to claim 4, wherein in the aqueous solution from which the lyophilized composition is prepared:
(A) the concentration of caspofungin or its salt is in a range of from about 30 mg/mL to about 50 mg/mL;
(B) the concentration ratio of trehalose to caspofungin is in a range of from about 4:1 to about 8:1; and
(C) the concentration of the acetate buffer is in a range of from about 20 mM to about 60 mM.

6. The lyophilized composition according to claim 5, wherein in the aqueous solution from which the lyophilized composition is prepared:
(A) the concentration of caspofungin or its salt is in a range of from about 30 mg/mL to about 50 mg/mL;
(B) the concentration of trehalose is in a range of from about 180 mg/mL to about 300 mg/mL; and
(C) the acetate buffer has a concentration in a range of from about 20 mM to about 60 mM.

7. A process for preparing a lyophilized anti-fungal composition with a moisture content of less than about 0.8 wt. %, which process comprises
(A) preparing an aqueous solution with a pH in a range of from about 5 to about 7 and comprising an effective amount of caspofungin or a pharmaceutically acceptable salt thereof, one or more non-reducing sugars having a glass transition temperature $T_g(s)$ of at least about 90° C., and an acetate buffer, wherein the concentration ratio, on a weight per unit volume basis, of the one or more non-reducing sugars to caspofungin is in a range of from about 1.1:1 to about 10:1 and wherein trehalose is the non-reducing sugar; and
(B) freeze-drying the aqueous solution to provide the lyophilized anti-fungal composition;
wherein the lyophilized anti-fungal composition with a moisture content of less than about 0.8 wt. % comprises:
(A) caspofungin, or a pharmaceutically acceptable salt thereof, in an effective amount;
(B) one or more non-reducing sugars having a glass transition temperature $T_g(s)$ of at least about 90° C.; and
(C) an acetate buffer in an amount effective to provide a pH in a range of from about 5 to about 7; and
wherein:
the weight ratio of the one or more non-reducing sugars to caspofungin is in a range of from about 1.1:1 to about 10:1; and
the composition has a glass transition temperature $T_g(c)$ of at least about 55° C.

8. The process according to claim 7, wherein Step A further comprises:
(a1) dissolving the one or more non-reducing sugars in water;
(a2) adding acetic acid and then adjusting the pH to be in a range of from about 4.5 to about 5.5 by addition of base;
(a3) adding caspofungin or its salt and adjusting the pH to a value in a range of from about 5 to about 7 by addition of more base; and
(a4) optionally filtering the resulting aqueous solution.

9. The process according to claim 8, wherein in the aqueous solution resulting from Step A the caspofungin or its salt has a concentration in a range of from about 5 mg/mL to about 200 mg/mL, and the concentration ratio of trehalose to caspofungin is in a range of from about 2:1 to about 10:1.

10. The process according to claim 9, wherein in the aqueous solution resulting from Step A the concentration of caspofungin or its salt is in a range of from about 30 mg/mL to about 50 mg/mL, and the concentration ratio of trehalose to caspofungin is in a range of from about 4:1 to about 8:1.

11. The process according to claim 7, wherein the moisture content of the resulting lyophilized composition is about 0.5 wt. % or less.

12. A lyophilized anti-fungal composition prepared by the process set forth in claim 7.

13. A kit comprising a first container having the lyophilized anti-fungal composition according to claim 1 and a second container having a parenterally acceptable solvent for reconstitution thereof.

14. A method of preparing an anti-fungal liquid formulation for parenteral administration, which comprises reconstituting the lyophilized anti-fungal composition according to claim 1 with a parenterally acceptable solvent to form an anti-fungal solution concentrate and then mixing the concentrate with a diluent comprising water to provide the formulation.

15. The method according to claim 14, wherein the parenterally acceptable solvent comprises water.

16. The method according to claim 15, wherein the parenterally acceptable solvent is selected from the group consisting of 0.9% Sodium Chloride Injection, Sterile Water for Injection, Bacteriostatic Water for Injection with methylparaben and propylparaben, and Bacteriostatic Water for Injection with 0.9% benzyl alcohol.

17. The method according to claim 16, wherein the diluent is 0.9%, 0.45% or 0.225% Sodium Chloride Injection or Lactated Ringer's Injection.

18. The method according to claim 17 wherein the concentrate contains from about 5 mg/mL to about 8 mg/mL of caspofungin, and the liquid formulation resulting from dilution of the concentrate contains from about 0.2 mg/mL to about 0.5 mg/mL of caspofungin.

19. An anti-fungal liquid dosage formulation for parenteral administration prepared by the method set forth in claim 14.

20. A method for the treatment or prophylaxis of a fungal infection which comprises parenterally administering to a subject in need thereof an anti-fungal liquid dosage formulation prepared by the method set forth in claim 14.

21. A kit comprising a first container having the lyophilized anti-fungal composition according to claim 12 and a second container having a parenterally acceptable solvent for reconstitution thereof.

22. A method of preparing an anti-fungal liquid formulation for parenteral administration, which comprises reconstituting the lyophilized anti-fungal composition according to claim 12 with a parenterally acceptable solvent to form an anti-fungal solution concentrate and then mixing the concentrate with a diluent comprising water to provide the formulation.

23. The method according to claim 22, wherein the parenterally acceptable solvent comprises water.

24. The method according to claim 23, wherein the parenterally acceptable solvent is selected from the group consisting of 0.9% Sodium Chloride Injection, Sterile Water for Injection, Bacteriostatic Water for Injection with methylparaben and propylparaben, and Bacteriostatic Water for Injection with 0.9% benzyl alcohol.

25. The method according to claim 24, wherein the diluent is 0.9%, 0.45% or 0.225% Sodium Chloride Injection or Lactated Ringer's Injection.

26. The method according to claim 25 wherein the concentrate contains from about 5 mg/mL to about 8 mg/mL of caspofungin, and the liquid formulation resulting from dilution of the concentrate contains from about 0.2 mg/mL to about 0.5 mg/mL of caspofungin.

27. An anti-fungal liquid dosage formulation for parenteral administration prepared by the method set forth in claim 22.

* * * * *

UNITED STATES PATENT AND TRADEMARK OFFICE
CERTIFICATE OF CORRECTION

PATENT NO.        : 8,551,942 B2                               Page 1 of 1
APPLICATION NO.   : 13/628592
DATED             : October 8, 2013
INVENTOR(S)       : Sachin Mittal et al.

It is certified that error appears in the above-identified patent and that said Letters Patent is hereby corrected as shown below:

On the Title Page, Item 72
Replace the misspelled last name of inventor "Sottivirat" with "Sotthivirat".

Signed and Sealed this
First Day of April, 2014

Michelle K. Lee
*Deputy Director of the United States Patent and Trademark Office*